(12) United States Patent
Staehlin et al.

(10) Patent No.: US 6,283,942 B1
(45) Date of Patent: *Sep. 4, 2001

(54) NEEDLE INSERTION GUIDE APPARATUS AND METHOD

(75) Inventors: John H. Staehlin, Lutherville; Guy Rubley, Arbutus, both of MD (US)

(73) Assignee: Volunteers for Medical Engineering, Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/001,194

(22) Filed: Dec. 30, 1997

(51) Int. Cl.[7] ............................. A61M 5/00; A61M 31/00
(52) U.S. Cl. ........................... 604/116; 604/117; 604/510
(58) Field of Search .................................... 604/116, 117, 604/174, 179, 500, 506, 507, 510; 600/461, 462, 464; 128/898

(56) References Cited
U.S. PATENT DOCUMENTS

| 4,062,237 | | 12/1977 | Fox . | |
|---|---|---|---|---|
| 4,527,569 | * | 7/1985 | Kolb | 128/660 |
| 4,635,644 | * | 1/1987 | Yagata | 128/660 |
| 4,667,679 | * | 5/1987 | Sahota | 128/663 |
| 4,733,661 | * | 3/1988 | Palestrant | 128/303 B |
| 4,911,173 | * | 3/1990 | Terwilliger | 128/662.06 |
| 4,966,589 | * | 10/1990 | Kaufman | 604/174 |
| 5,045,859 | | 9/1991 | Yetter . | |
| 5,167,630 | * | 12/1992 | Paul | 604/179 |
| 5,259,386 | * | 11/1993 | Sharkawy | 128/662.04 |
| 5,280,427 | * | 1/1994 | Magnusson et al. | 364/413.01 |
| 5,797,849 | * | 8/1998 | Vessely et al. | 600/461 |

* cited by examiner

Primary Examiner—Anhtuan T. Nguyen
Assistant Examiner—Michael J Hayes
(74) Attorney, Agent, or Firm—Finnegan, Henderson, Farabow, Garrett & Dunner, L.L.P.

(57) ABSTRACT

Disclosed is an apparatus and method for guiding a needle into a blood vessel of a patient. The apparatus is removably attached to a patient's arm, and uses the returns from transducer arrays to locate the blood vessel. The needle, positioned on the apparatus, is maneuvered in accordance with the transducer returns to ensure accurate penetration of the blood vessel.

24 Claims, 6 Drawing Sheets

NEEDLE INSERTION GUIDE APPARATUS AND METHOD

FIELD OF THE INVENTION

This invention relates to the field of medical care and more specifically to an apparatus and process for locating a blood vessel in a person and assisting in inserting a needle into the vessel.

BACKGROUND OF THE INVENTION

Medical professionals presently locate a blood vessel by palpitation or by blocking circulation in the vessel downstream from the needle insertion point, then looking for the bulging vessel. In many cases this procedure is unsuccessful in locating the vessel. Medical professionals may repeatedly stick the patient until they locate the vessel. Often, even when the vessel is successfully located, the needle penetrates too deeply, penetrating both walls of the vessel and striking a nerve. This problem is particularly acute when the patient is a small child. Or, a located vessel has a tendency to rotate or roll away from the needle as the medical professional attempts to insert it, further complicating the procedure.

SUMMARY OF THE INVENTION

Accordingly, the present invention is directed to a needle insertion guide apparatus that substantially obviates one or more of the problems due to limitations and disadvantages of the prior art. For example, the needle insertion guide assists in accurately locating a blood vessel within a patient. Thus, a medical professional need only penetrate the patient's skin once with a needle. Moreover, the needle insertion guide ensures proper alignment of the needle such that only one wall of the blood vessel will be penetrated. Also, consistent with the present invention, a rotatable vessel holder ensures that the blood vessel will not move during insertion of the needle.

To achieve these and other advantages and in accordance with the purpose of the invention, as embodied and broadly described, a guide for locating a blood vessel in a patient and guiding a needle consistent with the present invention includes a main support housing, means for removably securing the main support housing to the patient, a plurality of transducers attached to the main support housing for transmitting and receiving signals for locating the blood vessel, and at least one needle support attached to the main support housing.

To further achieve these advantages, a method for locating a blood vessel in a patient and guiding a needle into the located blood vessel is provided, the method includes the steps 3 of removably securing a main support housing to the patient, energizing a plurality of transducers attached to the main support housing for transmitting and receiving signals, locating the blood vessel based on the signals, and guiding a needle into the patient.

The accompanying drawings, which are incorporated in and constitute a part of this specification, illustrate several embodiments of the invention and, together with the description, serve to explain the principles of the invention.

Additional features and advantages of the invention will be set forth in the description that follows, and in part will be apparent from the description or may be learned by the practice of the invention. The objectives or other advantages of the invention will be realized and attained by the needle insertion guide particularly pointed out in the written descriptions and claims hereof, as well as in the accompanying drawings.

DETAILED DESCRIPTION OF THE PREFERRED EMBODIMENT

Reference will now be made in detail to the present preferred embodiment of the invention, an example of which is illustrated in the accompanying drawings. Wherever possible, the same reference numbers are used to refer to the same or like parts.

Figure 1:
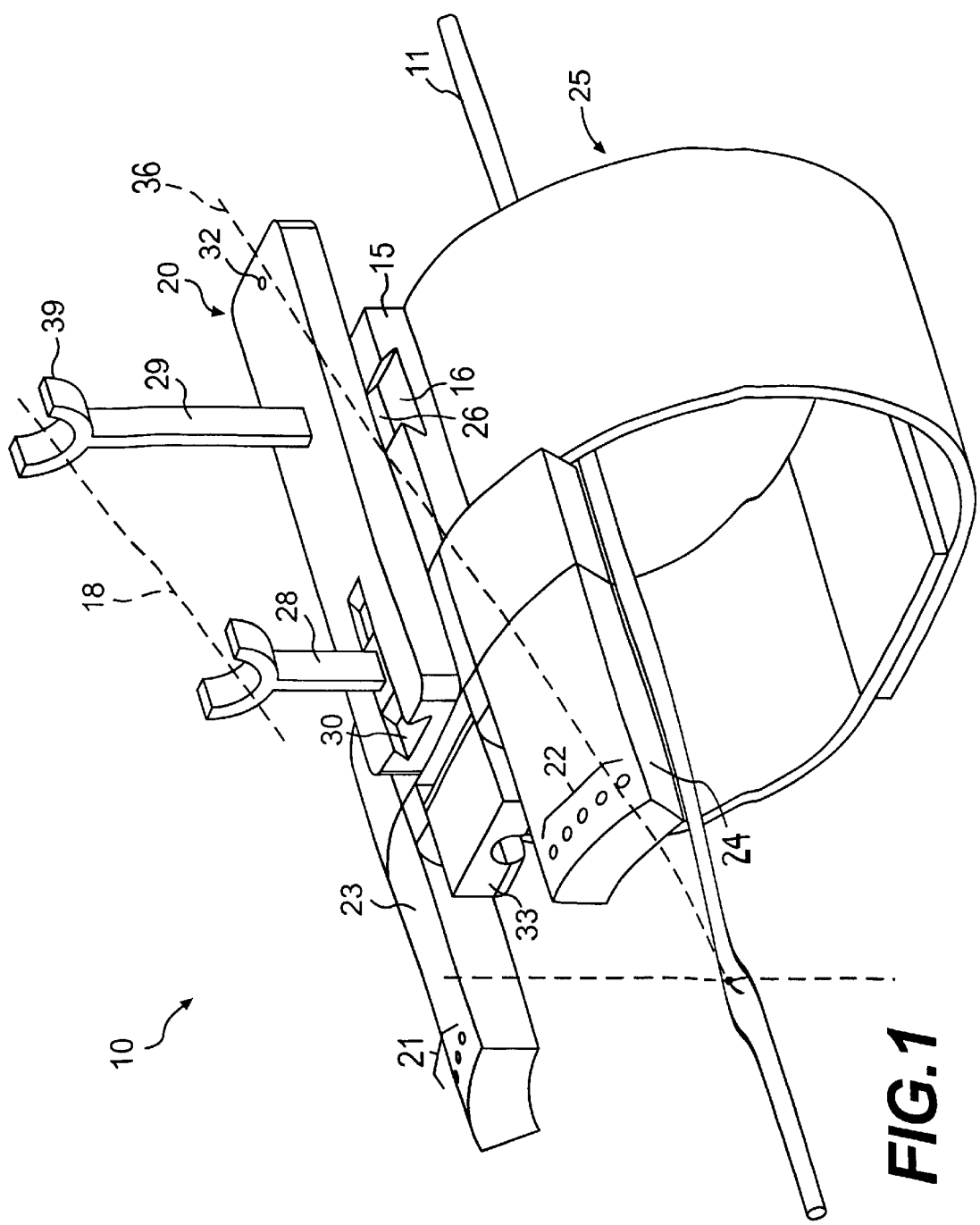
FIG. 1 is an isometric view of the needle insertion guide.
Figure 2:
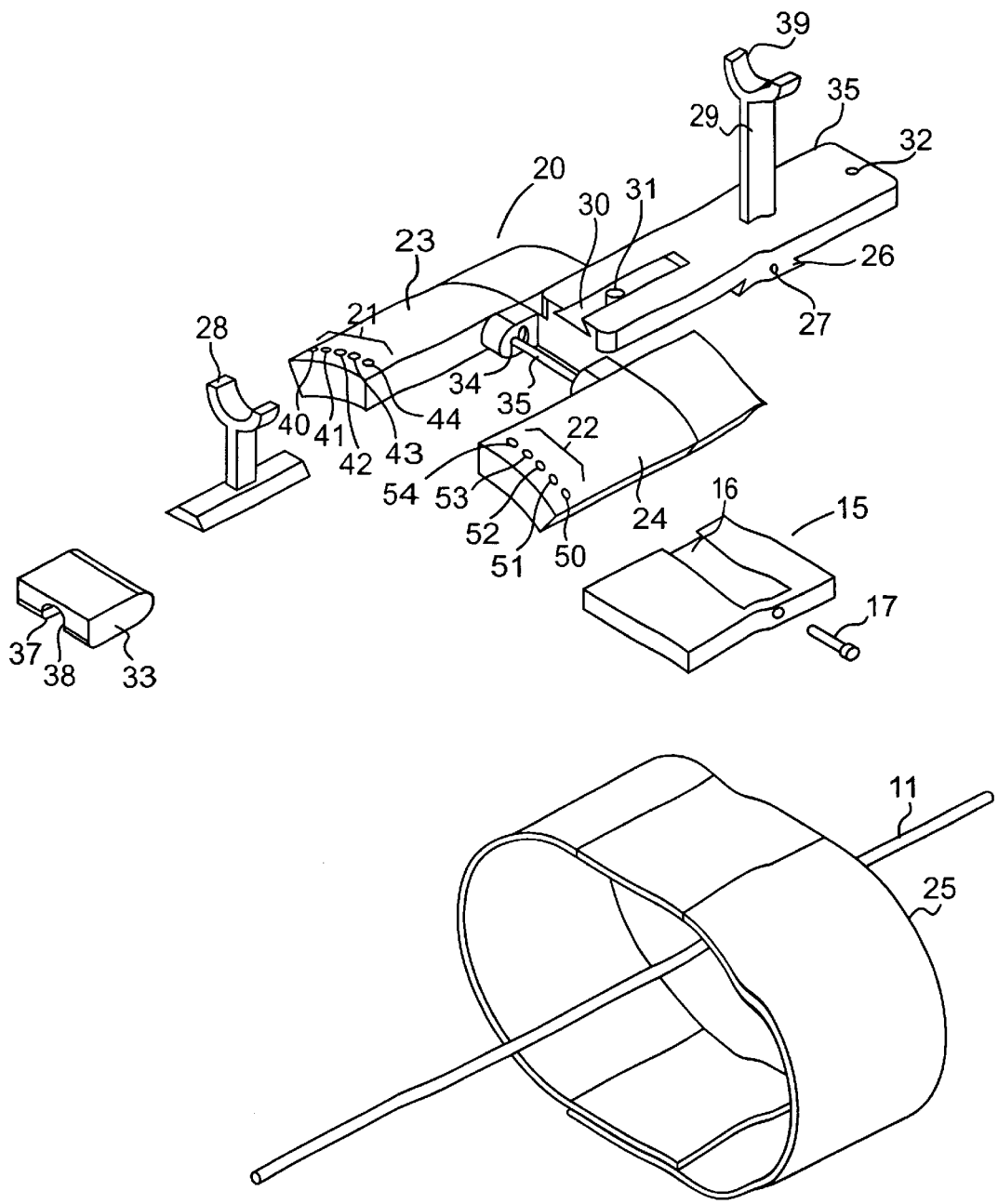
FIG. 2 is an exploded view of the needle insertion guide.
Figure 3:
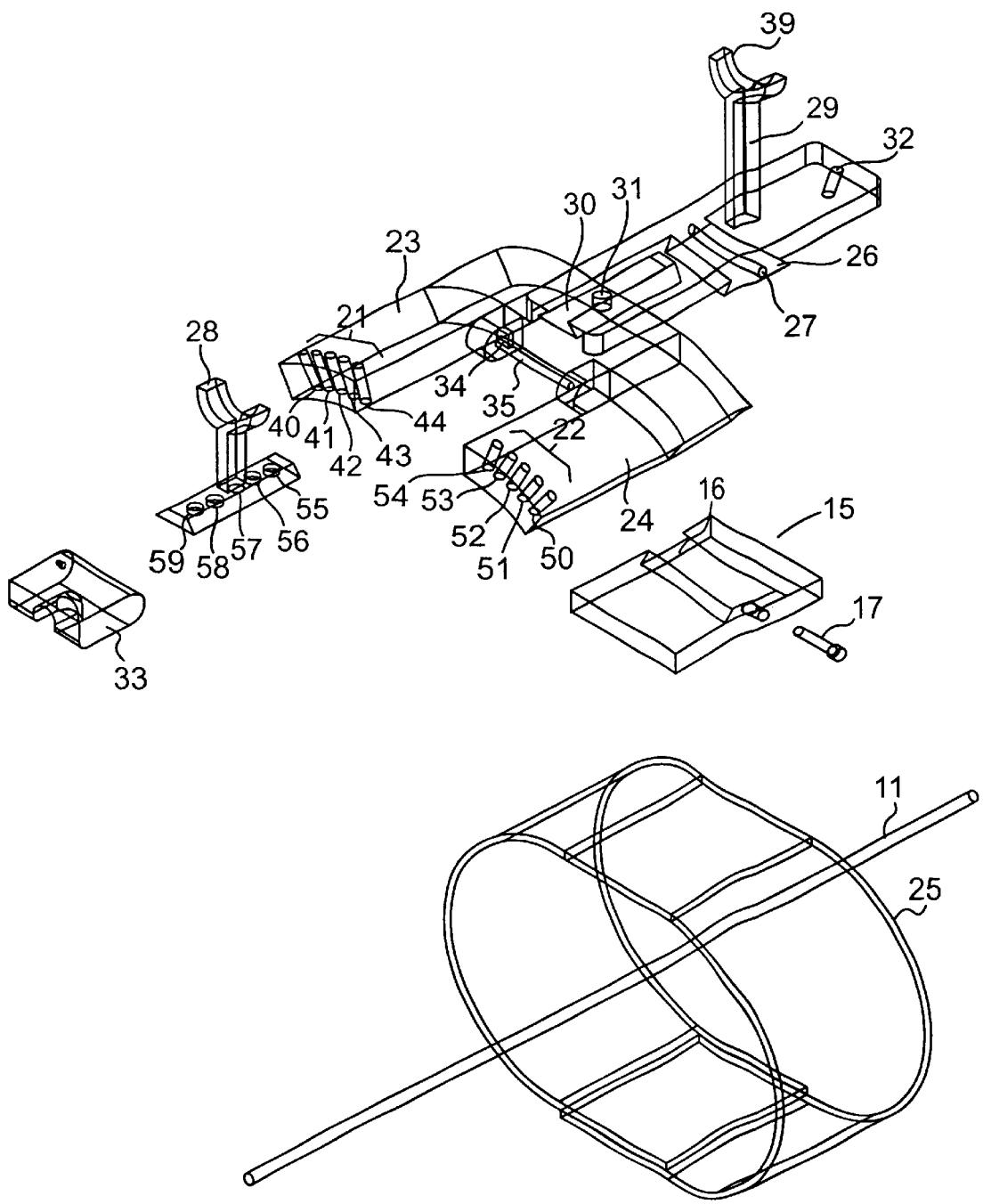
FIG. 3 is a wire-frame exploded view of the needle insertion guide.

A needle insertion guide 10, illustrated in FIGS. 1–3, aids in inserting a needle into a vessel 11. Needle insertion guide 10 includes a lateral slide 15 and a main support housing 20, which are secured to a patient by a securing strap 25. Securing strap 25 can be a flexible strap made of, for example, nylon, which is closed with Velcro®, snaps, etc., and can be of variable lengths to attach to different parts of the patient. Securing strap 25 can also have a fixed shape, such as a metallic or plastic bracelet.

Lateral slide 15 has a lateral channel 16 into which lateral guide 26 of main support housing 20 fits. Although lateral channel 16 is shown as a dovetail-shaped channel, any configuration that would maintain lateral guide 26 in the channel would be acceptable. Lateral slide 15 also has a screw 17 that fits into the side of lateral slide 15 and into hole 27 of lateral guide 26.

Main support housing 20 includes two transducer arrays 21 and 22 in transducer array supports 23 and 24. Transducer array 21 is made up of transducers 40, 41, 42, 43, and 44. Transducer array 22 is made up of transducers 50, 51, 52, 53, and 54. Main support housing 20 also has two needle supports 28 and 29. Needle support 28 fits into needle channel 30. Detent 31 in channel 30 allows needle support 28 to be locked in different positions in needle channel 30. Housing 20 also has an afl transducer 32, and a V-block 33 that is rotatably mounted on shaft 35. A ball detent 34 allows V-block 33 to be locked into place.

A computer (not shown) is linked to needle insertion guide 10 and causes signals to be sent and received from aft transducer 32 and the transducers in transducer arrays 21 and 22. The computer processes and displays information to aid in the positioning of needle insertion guide 10. It can be linked to guide 10 by cables, by radio link, or by any other suitable means. Alternatively, computing and display capabilities could be built into insertion guide 10 itself.

In operation, needle insertion guide 10 is initially placed on, for example, the arm of a patient with transducer arrays 21 and 22 pointing in the direction of the patient's elbow. Needle insertion guide 10 is positioned with a center line 36 of main support housing 20 roughly lined up with vessel 11, and then secured to the patient's arm with securing strap 25. Guide 10 is then set at its starting positions: needle support 28 in needle channel 30 is positioned at the center of its travel, and lateral guide 26 is positioned in the middle of its travel in lateral channel 16.

Figure 4:
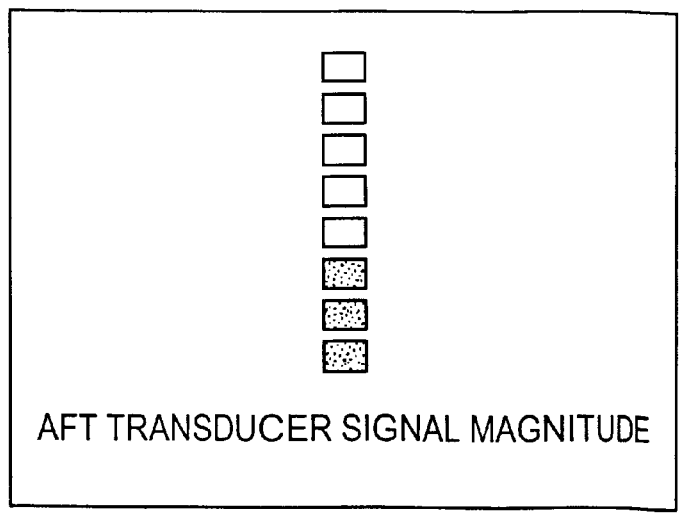
FIG. 4 illustrates a display showing aft transducer data consistent with the present invention.

To begin locating vessel 11 in the patient, the computer energizes aft transducer 32 to transmit and receive sonic energy. Although aft transducer 32 is shown positioned behind needle support 39, it could be positioned anywhere along the centerline of main support housing 20. The computer receives and processes the signals received by aft transducer 32. The computer then displays data that is monitored by the person operating guide 10. While monitoring the data, the user moves lateral guide 26 in lateral channel 16 by turning screw 17 until the signal received by af transducer 32 peaks. At this point, guide 10 is positioned coarsely above vessel FIG. 4 illustrates one example of the type of data the computer could display while the user laterally orients main housing 20. In this embodiment, the display consists of a bar graph showing the magnitude of the signal received by aft transducer 32. Alternatively, the computer could display the data in various other formats, such as numerically, or any other format that indicates when the signal received by aft transducer 32 has peaked.

Figure 5:
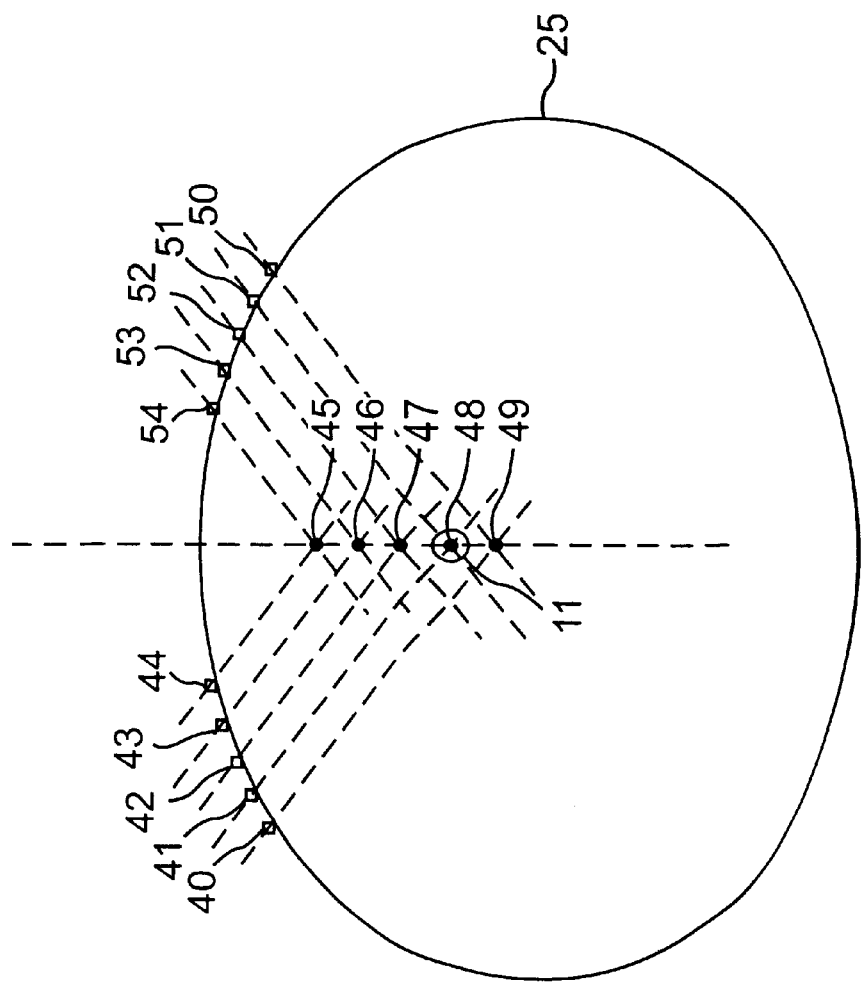
FIG. 5 is a front view of the transducers and securing strap of the needle insertion guide.

In order to further define the location and depth of vessel 11, the computer energizes transducers 40–44 and 50–54 in transducer arrays 21 and 22. Each transducer in array 21 has a corresponding transducer in array 22 (e.g., transducers 40, 41, 42, 43, and 44 in array 21 correspond to transducers 50, 51, 52, 53, and 54 in array 22, respectively). FIG. 5 shows a front view of transducer arrays 21 and 22. As shown, each pair of transducers is aligned such that the centerlines of sonar radiation intersect at specific depths beneath the patient's skin. Thus, transducers 40 and 50 radiate sonar energy along their respective center lines, which intersect at a point 49. Similarly, transducers 41 and 51 intersect at point 48; transducers 42 and 52 at point 47; transducers 43 and 53 at point 46; and transducers 44 and 54 at point 45. Each of the intersections are preferably spaced apart approximately the diameter of vessel 11.

Figure 6:
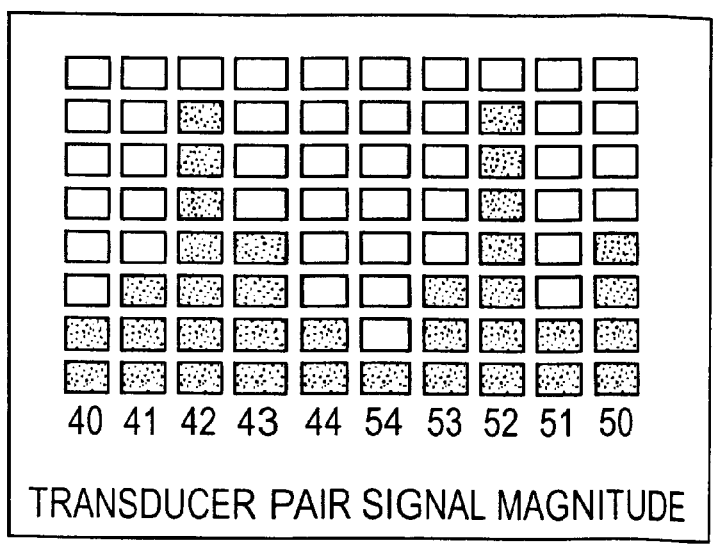
FIG. 6 illustrates a display showing transducer pair data consistent with the present invention.

The output of the pairs of transducers are used to fine-tune the location of needle centerline 18 with respect to vessel 11. This is accomplished by observing the level (e.g., as shown in FIG. 6, described below) of the returned signals in, for example, transducer 42 versus the level of transducer 52, and then turning screw 17 until the levels are equal.

The signal returns are also used to set the longitudinal position of needle support 28 in needle channel 30. To accomplish this, the computer compares the signal returns from each pair of transducers, and delineates the pair with the maximum signal return. As shown in the wire-frame drawing of FIG. 3, needle support 28 has five detent locks 55–59 that allow it to be locked into five different positions by detent 31. Each of the five positions corresponds to an intersection point of a transducer pair. Specifically, detent locks 55–59 correspond to points 45–49, respectively.

The person operating needle insertion guide 10 locks needle support 28 into the position corresponding to the maximum signal return from the transducer pairs. FIG. 6 illustrates one example of the type of data the computer could display while the user adjusts needle support 28. In this embodiment, the display consists of a bar graph showing the magnitude of the signals received by the transducer pairs. As shown, the pair made up of transducers 42 and 52 has the maximum signal returns. Since the signals generated by this pair intersect at point 47, needle support 28 would be locked at corresponding detent lock 57. As before, the computer could display the data in various other formats that indicate which transducer pair has the maximum signal return and, thus, which position needle support 28 should be locked in. The computer could also provide instructions to the user at each step.

At this point, needle insertion guide 10 is accurately aligned with vessel 11. To hold the vessel in place, V-block 33 may be rotated downward into contact with the skin. The sides 37 and 38 of V-block 33 hold the vessel, preventing it from moving laterally during the needle insertion process. Detent 34 is used to lock V-block 33 into place.

Now, the centerline 18 of a needle placed on needle supports 28 and 29 aligns with the point of intersection of the transducer pair having the maximum signal return. The needle is then moved forward to insert its point into vessel 11. The geometry of the arrangement ensures that the length from the needle point toothe stop surface on the needle body and the distance from the center of vessel 11 below the skin to the stop surface 39 on needle support 29, are the same. Thus, insertion will penetrate one wall of vessel 11, but not the second.

This needle insertion guide provides the maximum assurance that vessel 11 will be located on the initial attempt at insertion of the needle and will penetrate it to the proper depth. It will be obvious to those skilled in the art that various modifications and variations can be made in the needle insertion guide of the present invention without departing from the spirit or scope of the invention. For example, different kinds or quantities of transducers, or sensors, at different locations would accomplish the same effect as the preferred embodiment described above. Thus, it is intended that the present invention cover the modifications and variations of this invention provided they come within the scope of the appended claims and their equivalents.

We claim:

1. A guide for locating a blood vessel in a patient and guiding a needle into the located blood vessel, the guide comprising:

a main support housing;

means for removably securing the main support housing to the patient;

a plurality of transducers attached to the main support housing for generating signals for locating a three-dimensional location of the blood vessel;

means for converting the signals into a representation of the three-dimensional location of the blood-vessel; and at least one needle support attached to the main support housing for incremental adjustment and incremental positioning of the needle and the angle of entry of the needle in coordination with the representation of the three-dimensional location of the blood vessel.

2. The guide as claimed in claim 1, wherein the securing means comprises an adjustable strap.

3. The guide as claimed in claim 1, wherein the main support housing fits into a lateral channel in a cooperatively-configured lateral slide.

4. The guide as claimed in claim 1, wherein the main support housing includes two transducer supports, wherein a first plurality of transducers is located in one transducer support, and a second plurality of transducers is located in the other transducer support.

5. The guide as claimed in claim 4, wherein the plurality of transducers on each transducer support are arranged in a linear array generally perpendicular to a centerline of the main support housing.

6. The guide as claimed in claim 5, wherein each of the linear array of transducers are positioned on the transducer supports such that any one transducer of the array on a given transducer support has a corresponding counterpart transducer on the other transducer support, the corresponding signals of each pair of the counterpart transducers intersecting with each other at separate points spaced at different depths from the main support housing.

7. The guide as claimed in claim 6 wherein the points of intersection are spaced apart approximately the diameter of a blood vessel.

8. The guide as claimed in claim 1 wherein the main support housing includes an aft transducer located along a centerline of the main support housing.

9. The guide as claimed in claim 1, wherein the at least one needle support includes two Y-shaped needle supports, with one Y-shaped needle support being longer than the other.

10. The guide as claimed in claim 9, wherein the longer Y-shaped needle support is fixedly attached to the main support housing, and the shorter Y-shaped needle support is slidably attached to the main support housing.

11. The guide as claimed in claim 9, wherein one of the Y-shaped needle supports is slidably attached to the main support housing, and the other Y-shaped needle support is fixedly attached to the main support housing.

12. The guide as claimed in claim 1, further comprising means, attached to the main support housing, for holding the blood vessel in place once it is located.

13. The guide as claimed in claim 12, wherein the holding means comprises a V-block.

14. The guide as claimed in claim 13, wherein the V-block is rotatable.

15. The guide as claimed in claim 1, further comprising a transducer located along a centerline of the main support housing.

16. A method for locating a blood vessel in a patient and guiding a needle into the located blood vessel comprising the steps of:

removably securing a main support housing to the patient;

energizing a plurality of transducers, including an aft transducer, attached to the main support housing for transmitting and receiving signals;

adjusting a lateral position of the main support housing based upon a signal return from the aft transducer;

converting the signals into a representation of a three-dimensional location of the blood-vessel;

locating the blood vessel based on the representation of the three-dimensional location of the blood-vessel; and incrementally guiding a needle into the patient in coordination with the representation of the three-dimensional location of the blood-vessel.

17. A method for locating a blood vessel in a patient and guiding a needle into the located blood vessel comprising the steps of:

removably securing a main support housing to the patient;

energizing a plurality of transducers, including a first and a second plurality of transducers, attached to the main support housing for transmitting and receiving signals;

adjusting a longitudinal position of a needle support based upon signal returns from the first and second plurality of transducers;

converting the signals into a representation of a three-dimensional location of the blood-vessel;

locating the blood vessel based on the representation of the three-dimensional location of the blood-vessel; and incrementally guiding a needle into the patient in coordination with the representation of the three-dimensional location of the blood-vessel.

18. A method for locating a blood vessel in a patient and guiding a needle into the located blood vessel comprising the steps of:

removably securing a main support housing to the patient;

energizing a plurality of transducers attached to the main support housing for transmitting and receiving signals;

converting the signals into a representation of a three-dimensional location of the blood-vessel;

locating the blood vessel based on the representation of the three-dimensional location of the blood-vessel; and incrementally guiding a needle into the patient, including sliding the needle along two needle supports until its point penetrates one wall of the blood vessel, in coordination with the representation of the three-dimensional location of the blood-vessel.

19. A method for locating a blood vessel in a patient and guiding a needle into the located blood vessel comprising the steps of:

removably securing a main support housing to the patient;

energizing a plurality of transducers attached to the main support housing for transmitting and receiving signals;

adjusting a lateral position of the main support housing based upon a comparison of signal returns from at least one corresponding pair of transducers;

converting the signals into a representation of a three-dimensional location of the blood-vessel;

locating the blood vessel based on the representation of the three-dimensional location of the blood-vessel; and incrementally guiding a needle into the patient in coordination with the representation of the three-dimensional location of the blood-vessel.

20. A method for locating a blood vessel in a patient and guiding a needle into the located blood vessel comprising the steps of:

removably securing a main support housing to the patient;

energizing a plurality of transducers attached to the main support housing, including a centerline transducer positioned along a centerline of the main support housing, for transmitting and receiving signals;

laterally moving the main support housing until the centerline transducer is aligned with the blood vessel;

converting the signals into a representation of a three-dimensional location of the blood-vessel;

locating the blood vessel based on the representation of the three-dimensional location of the blood-vessel; and incrementally guiding a needle into the patient in coordination with the representation of the three-dimensional location of the blood-vessel.

21. The method of claim 20 wherein the energizing steps include the steps of energizing a plurality of transducers to determine the depth of the blood vessel.

22. A method for locating a blood vessel in a patient and guiding a needle into the located blood vessel comprising the steps of:

removably securing a support housing to the patient said support housing including a centerline transducer positioned along its centerline and two sets of a plurality of transducers arranged as linear arrays generally perpendicular to its centerline, with each transducer on one set having a corresponding counterpart transducer on the other;

energizing the centerline transducer to transmit and receive signals and moving the housing laterally to obtain a peak reading from the transducer, thereby locating the lateral position of a blood vessel;

maintaining the housing in position over the located blood vessel;

energizing the array transducers to determine the depth of the blood vessel; and guiding the needle into the blood vessel, according to the detected location of the blood vessel.

23. The method of claim 22 further comprising the step of positioning two needle supports on the housing and adjusting the longitudinal position of at least one needle support on the housing according to the signals received from said transducers.

24. The method of claim 23 further comprising the step of locking the needle supports into predetermined positions which correspond to peak signals received from two transducers on the arrays.

* * * * *